United States Patent [19]
Kondo et al.

[11] Patent Number: 5,965,649
[45] Date of Patent: Oct. 12, 1999

[54] POLYOXYETHYLENE ALKYL ESTER FATTY ACID AMIDE MODIFIED ORGANOPOLYSILOXANE COMPOSITION

[75] Inventors: Hidetoshi Kondo; Masahiro Takahashi, both of Chiba Prefecture, Japan

[73] Assignee: Dow Corning Toray Silicon Co., Ltd., Tokyo, Japan

[21] Appl. No.: 09/063,701

[22] Filed: Apr. 21, 1998

[30] Foreign Application Priority Data

Apr. 21, 1997 [JP] Japan .................................. 9-117576

[51] Int. Cl.⁶ ...................................................... C08K 5/09
[52] U.S. Cl. ........................ 524/320; 524/300; 524/378; 424/78.03
[58] Field of Search .................................. 524/300, 320, 524/378; 424/78.03

[56] References Cited

U.S. PATENT DOCUMENTS

| | | | |
|---|---|---|---|
| 4,973,620 | 11/1990 | Ona et al. | 524/292 |
| 5,262,087 | 11/1993 | Tachibana et al. | 424/78.03 |
| 5,863,982 | 1/1999 | Huang et al. | 524/300 |

*Primary Examiner*—Melvyn I. Marquis
*Attorney, Agent, or Firm*—James L. De Cesare

[57] ABSTRACT

A polyoxyethylene alkyl ether fatty acid amide modified organopolysiloxane composition is superior in terms of its feel in use, and in its surface-protecting characteristics, surface lubricating characteristics, and anti-static properties. The composition shows no degeneration over long periods of time. It is superior in terms of its mixing stability in cosmetic based agents, and in lustering agents, lubricating agents, defoaming agents, fiber treatment agents, and paint additives, and has a superior effect in improving their surface characteristics. The composition is a polyoxyethylene alkyl ether fatty acid amide modified organopolysiloxane composition containing an amidopolyether-modified organopolysiloxane and a polyoxyethylene alkyl ether fatty acid.

4 Claims, No Drawings

POLYOXYETHYLENE ALKYL ESTER FATTY ACID AMIDE MODIFIED ORGANOPOLYSILOXANE COMPOSITION

FIELD OF THE INVENTION

This invention is directed to a polyoxyethylene alkyl ether fatty acid amide modified organopolysiloxane composition. More particularly, it concerns a polyoxyethylene alkyl ether fatty acid amide modified organopolysiloxane composition which is superior in terms of mixing stability in cosmetic based agents, lustering agents, lubricating agents, defoaming agents, fiber treatment agents, or paint additives. The composition also makes it possible to obtain a favorable feel in use, favorable surface-protecting characteristics, surface lubricating characteristics, transparent mixing characteristics, and anti-static characteristics.

BACKGROUND OF THE INVENTION

Dimethylpolysiloxanes are common organopolysiloxanes. In addition, methylphenylpolysiloxanes, methylhydridopolysiloxanes, octamethylcyclotetrasiloxane, dimethylpolysiloxane-polyethylene glycol copolymers, and dimethylpolysiloxane-polypropylene glycol copolymers, are also known. Furthermore, various types of modified polysiloxanes such as methylstyrene-modified, olefin-modified, polyether-modified, alcohol-modified, fluorine-modified, amino-modified, mercapto-modified, epoxy-modified, carboxy-modified, and higher fatty acid-modified polysiloxanes, are available and are used in numerous fields.

For example, cosmetics have conventionally contained oil components for the purpose of preventing drying of the skin, and for the purpose of protecting the surfaces of hairs, since a light feel in use has been desired. In such cases and in recent years, dimethylpolysiloxanes have been widely used.

However, since dimethylpolysiloxanes are generally insufficiently compatible with water and other oily agents, problems have been encountered such as the fact that mixing them with cosmetics is difficult, and such mixtures tend to loose their stability. Furthermore, dimethylpolysiloxanes have a characteristic oily feeling, and therefore suffer from problems in terms of their feel in use. That is, such compounds lack a wet feel and have a strong "squeaky" feel. In addition, the compounds suffer from a drawback in that they are easily washed from the surfaces of the skin and hair.

Accordingly, a hair conditioner composition containing a polyoxyalkylene group containing polysiloxane (Japanese Patent Application Kokai No. 55-136214), and a hair conditioner composition containing an aminoalkyl methylpolysiloxane (Japanese Patent Application Kokai No. 56-45406) are known. However, the former composition suffers from poor retention, and the latter composition has a sticky feel so that its feel in use is unsatisfactory.

In addition, a method is known in which a composition is formed by dissolving an amino group containing organopolysiloxane and a polyoxyethylene fatty acid in toluene, and the composition is used as a fiber treatment agent (Japanese Patent Application Kokai No. 1-306682/U.S. Pat. No. 4,973, 620)).

A method is also known in which an emulsion consisting of a fatty acid amide modified organopolysiloxane, a surfactant, and water, is used as a cleaning agent for clothing. However, fatty acid amide modified polysiloxanes have a high degree of hydrophobicity and are inferior in terms of storage stability, with changes such as separation and aggregation occurring in the case of long term storage.

Accordingly, methods using fatty acid amide modified organopolysiloxanes as surface modifying agents have not been practical, and are believed to be unknown in the art.

BRIEF SUMMARY OF THE INVENTION

The object of this invention is to provide a polyoxyethylene alkyl ether fatty acid amide modified organopolysiloxane composition which is superior in terms of its feel in use, and in its surface-protecting characteristics, surface lubricating characteristics, and storage stability, so that the composition shows no degeneration even over long periods of time.

Another object of this invention is to provide such a composition which is superior in terms of its mixing stability in cosmetic based agents, and in lustering agents, lubricating agents, defoaming agents, fiber treatment agents, and paint additives, which makes it possible to obtain a favorable feel in use, and favorable transparent mixing characteristics, surface-protecting characteristics, surface lubricating characteristics, and anti-static characteristics.

These and other objects of the invention will become apparent from a consideration of the detailed description.

DETAILED DESCRIPTION OF THE INVENTION

In this invention, the above objects are achieved by the provision herein of a polyoxyethylene alkyl ether fatty acid amide modified organopolysiloxane composition containing (A) an amidopolyether-modified organopolysiloxane having the formula (1)

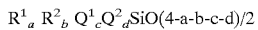

wherein a and d are 0 or a positive number, b and c are positive numbers with the proviso that a+b+c+d is 1.9 to 2.2 inclusive, $R^1$ is a hydrogen atom, a hydroxy group, or an unsubstituted or substituted monovalent hydrocarbon group with 1 to 6 carbon atoms, $R^2$ is a monovalent hydrocarbon group with 1 to 6 carbon atoms, $Q^1$ is a group having the formula (2)

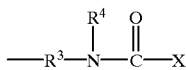

or having the formula (3)

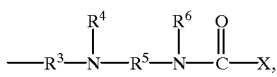

wherein $R^3$ and $R^5$ are divalent hydrocarbon groups with 2 to 18 carbon atoms, $R^4$ and $R^6$ are hydrogen atoms or monovalent hydrocarbon groups with 1 to 6 carbon atoms, X is a group having the formula (4)

wherein e and f are respectively 0 or 1, g and h are 0 or positive integers equal to or greater than 1, $R^7$ is a divalent hydrocarbon group with 2 to 18 carbon atoms, $R^8$ is a divalent hydrocarbon group with 3 to 10 carbon atoms, Y is a hydrogen atom, a monovalent hydrocarbon group with 1 to 18 carbon atoms, an acyl group, or an isocyano group, $Q^2$ is a group having the formula (5)

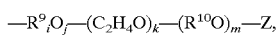

wherein i and j are respectively 0 or 1, k is a positive integer equal to or greater than 1, m is 0 or a positive integer equal to or greater than 1, $R^9$ is a divalent hydrocarbon group with 2 to 18 carbons atoms, $R^{10}$ is a divalent hydrocarbon group with 3 to 10 carbon atoms, and Z is a hydrogen atom, a monovalent hydrocarbon group with 1 to 18 carbon atoms, an acyl group or an isocyano group; with the proviso that d and g are not simultaneously equal to zero; and (B) a polyoxyethylene alkyl ether fatty acid;

the content of component (B) being in the range of 0.001 to 20 percent by weight.

The organopolysiloxane component (A) used in this invention is an organopolysiloxane which has amido groups and polyoxyethylene groups as indicated by formula (1).

In formula (1), $R^1$ is a hydrogen atom, a hydroxy group, or a monovalent hydrocarbon group with 1 to 6 carbon atoms. Some examples of monovalent hydrocarbon groups include alkyl groups such as methyl, ethyl, propyl, butyl, pentyl, or hexyl; aryl groups such as phenyl, tolyl, or xylyl; aralkyl groups such as benzyl or phenethyl; and halo-substituted alkyl groups such as 3-chloropropyl or 3,3,3-trifluoropropyl.

$R^2$ in formula (1) is a monovalent hydrocarbon group with 1 to 6 carbon atoms such as methyl groups, ethyl groups, propyl groups, butyl groups, pentyl groups, hexyl groups, vinyl groups and phenyl groups.

$Q^1$ in formula (1) is an amide-group-containing divalent organic group expressed by formulas (2) or (3).

$R^3$ and $R^5$ in these formulas are divalent hydrocarbon groups with 2 to 18 carbon atoms such as ethylene groups, propylene groups, butylene groups, isobutylene groups, pentamethylene groups, octamethylene groups, decamethylene groups, dodecamethylene groups, and cyclohexyl groups.

$R^4$ and $R^6$ in these formulae are hydrogen atoms or monovalent hydrocarbon groups. Examples of such monovalent hydrocarbon groups include alkyl groups such as methyl groups, ethyl groups, propyl groups, butyl groups, pentyl groups or hexyl groups; aryl groups such as phenyl groups, tolyl groups, or xylyl groups; aralkyl groups such as benzyl groups or phenethyl groups; and halo-substituted alkyl groups such as 3-chloropropyl groups or 3,3,3-trifluoropropyl groups.

X in formulas (2) and (3) is a monovalent organic group having formula (4).

$R^7$ is a divalent hydrocarbon group with 2 to 18 carbon atoms. Examples of such divalent hydrocarbon groups include ethylene groups, propylene groups, butylene groups, isobutylene groups, pentamethylene groups, octamethylene groups, decamethylene groups, dodecamethylene groups, and cyclohexyl groups.

$R^8$ is a divalent hydrocarbon group with 3 to 10 carbon atoms such as propylene, isopropylene, butylene, and isobutylene.

Y is a group selected from hydrogen atoms, alkyl groups, acyl groups, and isocyano groups. Examples of such groups include methyl groups, ethyl groups, propyl groups, acetyl groups, and propionyl groups.

$Q^2$ in formula (1) is a polyoxyalkylene-group-containing monovalent organic group with formula (5).

In formula (5), $R^9$ is a divalent hydrocarbon group with 2 to 18 carbon atoms such as an ethylene group, propylene group, butylene group, isobutylene group, pentamethylene group, octamethylene group, decamethylene group, dodecamethylene group, and cyclohexyl group.

$R^{10}$ is a divalent hydrocarbon group with 3 to 10 carbon atoms such as a propylene group, isopropylene group, butylene group, and isobutylene group.

Z is a group selected from hydrogen atoms, alkyl groups, acyl groups, and isocyano groups. Examples of such groups include methyl groups, ethyl groups, propyl groups, acetyl groups, and 5 propionyl groups.

In compounds of formula (1), it is desirable that c be in the range of 0.001 to 1. If c is less than 0.001, retention on the skin and hair is poor. If c exceeds 1, sufficient smoothness and softness cannot be obtained.

It is also desirable that g or k be 2 to 20. If these values are less than 2, sufficient anti-static properties and mixing stability, and satisfactory feel in use when wet, cannot be obtained. If these values exceed 20, the water solubility is increased so that retention drops.

The hydrophilicity of the composition of this invention can be varied by adjusting the content of polyethylene oxide groups, so that mixing stability with various types of final compositions can be optimized. In addition, the solubility/deposition characteristics in systems can be controlled in accordance with variations in the ambient surfactant concentration under various conditions of use.

The molecular structure of component (A) is not limited to a linear structure, but it may also be branched, cyclic or have a network-form.

Compounds shown below represent suitable of such polysiloxanes containing amido groups and polyoxyethylene groups.

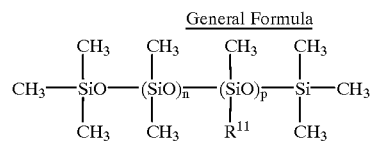

General Formula

In the above formula, $R^{11}$ is $-(CH_2)_3NHCO(CH_2)_qO(CH_2CH_2O)_r(CH_2)_sH$; n is 10 to 1,000, p is 1 to 100, q is 1 to 100, r is 2 to 20, and s is 0 to 20.

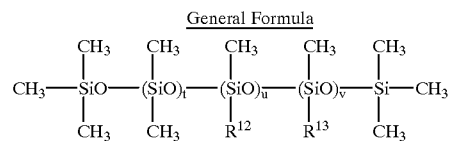

General Formula

In the above formula, $R^{12}$ is $-(CH_2)_3NH(CH_2)_2NHCO(CH_2)_wH$, $R^{13}$ is $-(CH_2)_3(CH_2CH_2O)_x(CH_2CHCH_3O)_y(CH_2)_zH$; t is 10, 1,000, u is 1 to 100, v is 1 to 100, w is 1 to 20, x is 2 to 20, y is 0 to 20 and z is 0 to 20.

The compounds shown below are specific examples.

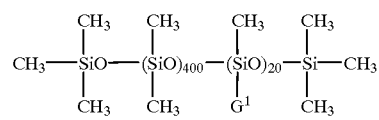

In the above formula, $G^1$ is $-(CH_2)_3NHCOCH_2O(CH_2CH_2O)_4C_{12}H_{25}$).

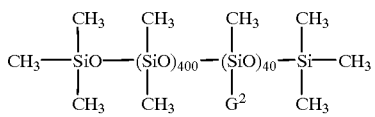

In the above formula, $G^2$ is —$(CH_2)_3NH(CH_2)_2NHCO(CH_2)_3O(CH_2CH_2O)_{10}C_{12}H_{25})$.

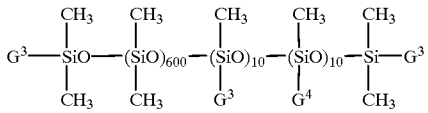

In the above formula, $G^3$ is —$(CH_2)_3O(CH_2CH_2O)_{10}(CH_2CHCH_3O)_{10}H$, and $G^4$ is —$(CH_2)_3NHCO(CH_2)_3O(CH_2CH_2O)_6C_{10}H_{21})$.

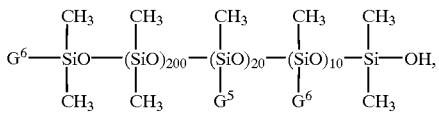

In the above formula, $G^5$ is —$(CH_2)_3O(CH_2CH_2O)_{10}COCH_3$, and $G^6$ is —$(CH_2)_3NH(CH_2)_2NHCOC_{16}H_{33})$ Polyoxyethylene alkyl ether fatty acids which can be used as component (B) in this invention include compounds expressed by the formula $HOOC(CH_2)\alpha$—$O$—$(CH_2CH_2O)\beta$—$(CH_2)\gamma H$ wherein alpha is 1 to 20, beta is 2 to 20, and gamma is 0 to 20.

Examples of such compounds include polyoxyethylene lauryl ether acetic acids, polyoxyethylene stearyl ether acetic acids, polyoxyethylene oleyl ether acetic acids, polyoxyethylene cetyl ether acetic acids, polyoxyethylene tridecyl ether acetic acids, polyoxyethylene polyoxypropylene lauryl ether acetic acids, polyoxyethylene lauryl ether lauric acids, and polyoxyethylene lauryl ether stearic acids. The content of component (b) is in the range of 0.001 to 20 percent by weight.

The composition of this invention can be manufactured by using an amount of component (B) equal to the reaction equivalent or greater in an amidization reaction, or by adding an optimal amount of (B) following synthesis of component (A).

Component (B) shows surfactant performance and acts to reinforce anti-static properties. In addition, it improves the mixing characteristics where mixing with the composition is indicated in the examples of application of the composition of this invention.

In addition to components (A) and (B), there can be used other surface-modifying agent additives such as dimethylpolysiloxanes, octamethylcyclotetrasiloxane, vaseline, or liquid paraffins. Such optional additives may be mixed with the composition of this invention provided they have no deleterious effect on the composition.

When the surface-modifying agent composition of this invention is used in cosmetics, lubricating agents, lustering agents, defoaming agents, fiber treatment agents, and paints, and when it is manufactured by adding other additives to it; or when the surface-modifying agent of this invention is added to cosmetics, lubricating agents, lustering agents, defoaming agents, fiber treatment agents, or paints, to improve their surface-modifying characteristics; it is desirable that the content of the surface-modifying agent composition of this invention be present in the range of 0.1 to 99.9 percent by weight, preferably 1 to 99 percent by weight.

The composition of this invention is superior in terms of its anti-static properties, surface feel, surface protective characteristics, surface lubricating properties, and storage stability, and it shows no degeneration even over long periods of time.

Furthermore, the composition shows good mixing stability with cosmetics, lubricating agents, lustering agents, defoaming agents, fiber treatment agents, and paints, and it can therefore greatly improve the surface-modifying characteristics of such products by being mixed with such products.

Accordingly, the composition of this invention is useful as a surface-modifying additive for improving the surface-modifying characteristics of cosmetics, lubricating agents, lustering agents, defoaming agents, fiber treatment agents, and paints.

EXAMPLES

The invention will be described in detail below by means of practical examples of application and reference examples. In addition, the raw materials and evaluation methods used herein are explained below.

Raw Materials

An amino-modified polysiloxane having the formula

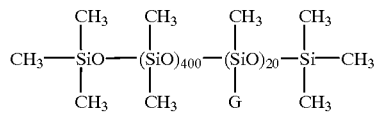

where G was $(CH_2)_3NH_2$.

A dimethylpolysiloxane having the formula

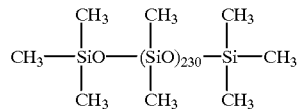

Evaluation Methods

Storage Stability Test 50 cc of the prepared surface-modifying agent composition was placed in a transparent glass bottle, and was allowed to stand quietly for one day at a temperature of 50° C. Afterward, the condition of the composition was observed by visual inspection. Evaluation criteria were:

A: uniform; showed no change.

B: showed a slight separation of oily matter.

C: oily matter separated.

D: oil droplets generated and separated.

Test of Anti-Static Properties 15 g of hair with a length of 15 cm was formed into a bundle, and was coated overall with the prepared surface-modifying agent. The sample was rinsed with running water for 30 seconds, after which the moisture was wiped away with a towel. The hair sample was dried with a drier, and then rubbed 100 times with a polyvinyl chloride resin plate. The condition of the hair sample was evaluated using the following evaluation criteria:

A: hair sample did not show any spreading.

B: hair sample showed slight spreading.

C: hair sample was spread.

D: hair sample stood up in opposite directions.

Test of Feel in the Case of Skin Cosmetic Use

The inside surface of the forearms of 10 panel members were uniformly coated with the surface-modifying agent prepared, and the softness of the skin, smoothness, and feel of oiliness, were subjectively evaluated using the following evaluation criteria:

A: extremely good.
B: somewhat good.
C: somewhat poor.
D: extremely poor.

Test of Feel in the Case of Hair Cosmetic Use 15 g of hair with a length of 15 cm was formed into a bundle, and was coated overall with the prepared surface-modifying agent. The sample was rinsed with running water for 30 seconds, after which the moisture was wiped away with a towel. The hair sample in a wet state was combed with a comb, and the feel of "squeakiness" was subjectively evaluated using the evaluation criteria shown below. Subsequently, the moisture was wiped away with a towel, and the hair sample was dried with a drier, after which the softness, smoothness, and oily feel, of the hair were subjectively evaluated using the following evaluation criteria:

A: extremely good.
B: somewhat good.
C: somewhat poor.
D: extremely poor.

Reference Example 1

300 g (0.0093 mol) of an amino-modified organopolysiloxane having a viscosity of about 1000 cs and having the formula the formula

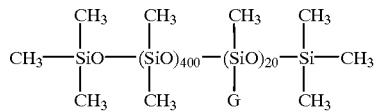

where G was $(CH_2)_3NH_2$, and 100 g (0.238 mol) of polyoxyethylene (4) lauryl ether acetic acid, were placed in a 1-liter four-necked flask equipped with an agitator, a thermometer, a nitrogen gas blowing tube, and a water separator. The mixture was reacted for 2 hours at 150° C. The reaction product obtained was a mixture containing a polyoxyethylene alkyl ether fatty acid amide modified organopolysiloxane expressed by the formula (5):

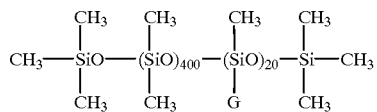

where G was $—(CH_2)_3NHCOCH_2O(CH_2CH_2O)_4C_{12}H_{25}$, and polyoxyethylene (4) lauryl ether acetic acid. The content of polyoxyethylene (4) lauryl ether acetic acid was 5.4 percent by weight.

Practical Example 1

10 parts by weight of the composition obtained in Reference Example 1, 10 parts by weight of lanolin, 40 parts by weight of octamethylcyclotetrasiloxane, and 40 parts by weight of liquid paraffin, were uniformly mixed to produce a composition. The composition was subjected to a storage stability test, a test of its anti-static properties, and a test of the feel of the composition in its use as a skin cosmetic. Measured results are shown in Table 1 below.

Comparative Example 1

A composition was prepared in the same manner as in Practical Example 1, except that an amino-modified polysiloxane was added, instead of the composition of Reference Example 1 used in Practical Example 1. The characteristics of the composition were evaluated in the same manner as in Practical Example 1. Measured results are shown in Table 1 below.

Comparative Example 2

A composition was prepared in the same manner as in Practical Example 1, except that a dimethylpolysiloxane was added, instead of the composition of Reference Example 1 used in Practical Example 1. The characteristics of the composition were evaluated in the same manner as in Practical Example 1. Measured results are shown in Table 1 below.

Comparative Example 3

A composition was prepared in the same manner as in Practical Example 1, except that vaseline was added, instead of the composition of Reference Example 1 used in Practical Example 1. The characteristics of the composition were evaluated in the same manner as in Practical Example 1. Measured results are shown in Table 1 below.

TABLE 1

| Items | Practical Example 1 | Comparative Example 1 | Comparative Example 2 | Comparative Example 3 |
|---|---|---|---|---|
| Composition | | | | |
| Composition of Reference Example 1 | 10 | | | |
| Amino-modified polysiloxane | | 10 | | |
| Dimethylpolysiloxane | | | 10 | |
| Vaseline | | | | 10 |
| Lanolin | 10 | 10 | 10 | 10 |
| Octamethylcyclotetrasiloxane | 40 | 40 | 40 | 40 |
| Liquid paraffin | 40 | 40 | 40 | 40 |
| Evaluation results | | | | |
| Storage stability | A | A | A | D |
| Anti-static properties | A | C | C | D |
| Softness | A | A | B | D |
| Smoothness | A | B | C | D |
| Oily feeling | A | C | C | D |

Practical Example 2

10 parts by weight of the composition of Reference Example 1, 0.5 parts by weight of stearic acid, 1.5 parts by weight of cetanol, 3 parts by weight of vaseline, 2 parts by weight of lanolin alcohol, 2 parts by weight of a polyoxyethylene (10) monooleate, 3 parts by weight of propylene glycol, 1 part by weight of triethanolamine, and 75 parts by weight of water, were uniformly mixed to produce a composition. The composition was subjected to a storage stability test, a test of its anti-static properties, and a test of its feel in use as a skin cosmetic. Measured results are shown in Table 2 below.

Comparative Example 4

A composition was prepared in the same manner as in Practical Example 2, except that an amino-modified polysiloxane was added, instead of the composition of Reference Example 1 used in Practical Example 2. The characteristics of the composition were evaluated in the same manner as in Practical Example 2. Measured results are shown in Table 2 below.

Comparative Example 5

A composition was prepared in the same manner as in Practical Example 2, except that a dimethylpolysiloxane was added, instead of the composition of Reference Example 1 used in Practical Example 2. The characteristics of the composition were evaluated in the same manner as in Practical Example 2. Measured results are shown in Table 2 below.

TABLE 2

| Item | Practical Example 2 | Comparative Examples | |
|---|---|---|---|
| | | 4 | 5 |
| Composition | | | |
| Emulsion composition of Reference Example 1 | 10 | | |
| Amino-modified polysiloxane | | 10 | |
| Dimethylpolysiloxane | | | 10 |
| Stearic acid | 0.5 | 0.5 | 0.5 |
| Cetanol | 1.5 | 1.5 | 1.5 |
| Vaseline | 3 | 3 | 3 |
| Lanolin alcohol | 2 | 2 | 2 |
| Polyoxyethylene (10) monooleate | 2 | 2 | 2 |
| Propylene glycol | 3 | 3 | 3 |
| Triethanolamine | 1 | 1 | 1 |
| Water | 75 | 75 | 75 |
| Evaluation results | | | |
| Storage stability | A | D | C |
| Anti-static properties | A | B | C |
| Softness | A | C | B |
| Smoothness | A | C | B |
| Oily feeling | A | C | B |

Practical Example 3

4 parts by weight of the composition of Reference Example 1, 4 parts by weight of stearyltrimethylammonium chloride, 3 parts by weight of cetanol, 5 parts by weight of propylene glycol, and 84 parts by weight of water, were uniformly mixed to produce a composition. The composition was subjected to a storage stability test, a test of its anti-static properties, and a test of the feel of the composition in its use as a hair cosmetic. Measured results are shown in Table 3 below.

Comparative Example 6

A composition was prepared in the same manner as in Practical Example 3, except that an amino-modified polysiloxane was added, instead of the composition of Reference Example 1 used in Practical Example 3. The characteristics of the composition were evaluated in the same manner as in Practical Example 3. Measured results are shown in Table 3 below.

Comparative Example 7

A composition was prepared in the same manner as in Practical Example 3, except that a dimethylpolysiloxane was added, instead of the composition of Reference Example 1 used in Practical Example 3. The characteristics of the composition were evaluated in the same manner as in Practical Example 3. Measured results are shown in Table 3 below.

TABLE 3

| Item | Practical Example 3 | Comparative Examples | |
|---|---|---|---|
| | | 6 | 7 |
| Composition | | | |
| Emulsion composition of Reference Example 1 | 4 | | |
| Amino-modified polysiloxane | | 4 | |
| Dimethylpolysiloxane | | | 4 |
| Stearyltrimethylammonium chloride | 4 | 4 | 4 |
| Cetanol | 3 | 3 | 3 |
| Propylene glycol | 5 | 5 | 5 |
| Water | 84 | 84 | 84 |
| Evaluation results | | | |
| Storage stability | A | A | B |
| Anti-static properties | A | B | C |
| "Squeaky" feel when wet | A* | D* | C* |
| Softness | A | C | B |
| Smoothness | A | B | C |
| Oily feeling | A | B | C |

In Table 3, A* indicates no "squeaky" feel, D* indicates a strong "squeaky" feel, and C* indicates some "squeaky" feel.

Thus, the composition of this invention can be seen to be superior in terms of its surface feel, and its surface protective characteristics, surface lubricating properties, and anti-static properties. It shows no degeneration even over long periods of time. Furthermore, the composition shows good mixing stability with cosmetics, lubricating agents, lustering agents, defoaming agents, fiber treatment agents, and paints, and has a superior effect in improving their surface characteristics.

Other variations may be made in compounds, compositions, and methods described herein without departing from the essential features of the invention. The embodiments of the invention specifically illustrated herein are exemplary only and not intended as limitations on their scope except as defined in the appended claims.

We claim:

1. A polyoxyethylene alkyl ether fatty acid amide modified organopolysiloxane composition comprising (A) an amidopolyether-modified organopolysiloxane having the formula (1)

$$R^1_a R^2_b Q^1_c Q^2_d SiO(4-a-b-c-d)/2$$

wherein a and d are 0 or a positive number, b and c are positive numbers with the proviso that a+b+c+d is 1.9 to 2.2 inclusive, $R^1$ is a hydrogen atom, a hydroxy group, or an unsubstituted or substituted monovalent hydrocarbon group with 1 to 6 carbon atoms, $R^2$ is a monovalent hydrocarbon group with 1 to 6 carbon atoms, $Q^1$ is a group having the formula (2)

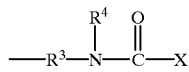

or having the formula (3)

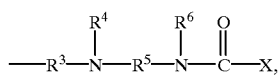

wherein $R^3$ and $R^5$ are divalent hydrocarbon groups with 2 to 18 carbon atoms, $R^4$ and $R^6$ are hydrogen atoms or monovalent hydrocarbon groups with 1 to 6 carbon atoms, X is a group having the formula (4)

$$-R^7_e O_f-(C_2H_4O)g-(R^8O)_h-Y$$

wherein e and f are respectively 0 or 1, g and h are 0 or positive integers equal to or greater than 1, $R^7$ is a divalent hydrocarbon group with 2 to 18 carbon atoms, $R^8$ is a divalent hydrocarbon group with 3 to 10 carbon atoms, Y is a hydrogen atom, a monovalent hydrocarbon group with 1 to 18 carbon atoms, an acyl group, or an isocyano group, $Q^2$ is a group having the formula (5)

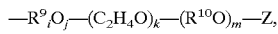

wherein i and j are respectively 0 or 1, k is a positive integer equal to or greater than 1, m is 0 or a positive integer equal to or greater than 1, $R^9$ is a divalent hydrocarbon group with 2 to 18 carbons atoms, $R^{10}$ is a divalent hydrocarbon group with 3 to 10 carbon atoms, and Z is a hydrogen atom, a monovalent hydrocarbon group with 1 to 18 carbon atoms, an acyl group or an isocyano group; with the proviso that d and g are not simultaneously equal to zero; and (B) a polyoxyethylene alkyl ether fatty acid, the content of component (B) in the composition being in the range of about 0.001 to 20 percent by weight.

2. The composition according to claim 1 wherein the amidopolyether-modified organopolysiloxane (A) has the formula:

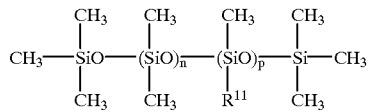

wherein $R^{11}$ is $-(CH_2)_3NHCO(CH_2)_qO(CH_2CH_2O)_r(CH_2)_sH$; n is 10 to 1,000, p is 1 to 100, q is 1 to 100, r is 2 to 20, and s is 0 to 20;

or the formula:

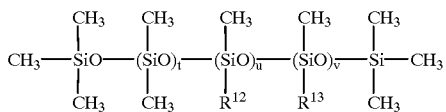

wherein $R^{12}$ is $-(CH_2)_3NH(CH_2)_2NHCO(CH_2)_wH$, $R^{13}$ is $-(CH_2)_3(CH_2CH_2O)_x(CH_2CHCH_3O)_y(CH_2)_zH$; t is 10, 1,000, u is 1 to 100, v is 1 to 100, w is 1 to 20, x is 2 to 20, y is 0 to 20 and z is 0 to 20.

3. The composition according to claim 1 wherein the polyoxyethylene alkyl ether fatty acid has the formula $HOOC(CH_2)\alpha-O-(CH_2CH_2O)\beta-(CH_2)\gamma H$ wherein alpha is 1 to 20, beta is 2 to 20, and gamma is 0 to 20.

4. The composition according to claim 3 wherein the polyoxyethylene alkyl ether fatty acid is selected from the group consisting of polyoxyethylene lauryl ether acetic acids, polyoxyethylene stearyl ether acetic acids, polyoxyethylene oleyl ether acetic acids, polyoxyethylene cetyl ether acetic acids, polyoxyethylene tridecyl ether acetic acids, polyoxyethylene polyoxypropylene lauryl ether acetic acids, polyoxyethylene lauryl ether lauric acids, and polyoxyethylene lauryl ether stearic acids.

* * * * *